United States Patent [19]

Fischell et al.

[11] Patent Number: 4,898,575
[45] Date of Patent: Feb. 6, 1990

[54] GUIDE WIRE FOLLOWING TUNNELING CATHETER SYSTEM AND METHOD FOR TRANSLUMINAL ARTERIAL ATHERECTOMY

[75] Inventors: Robert E. Fischell, Silver Spring, Md.; Tim A. Fischell, Palo Alto, Calif.

[73] Assignee: MedInnovations, Inc., Dayton, Md.

[21] Appl. No.: 205,541

[22] Filed: Jun. 10, 1988

Related U.S. Application Data

[63] Continuation of Ser. No. 91,311, Aug. 31, 1987, abandoned, which is a continuation of Ser. No. 874,140, Jun. 13, 1986, abandoned.

[51] Int. Cl.⁴ ............................................. A61B 17/32
[52] U.S. Cl. ...................................... 604/22; 606/159
[58] Field of Search ................ 128/305, 304, 751–758, 128/348.1, 344, 305.1, 310; 604/22

[56] References Cited

U.S. PATENT DOCUMENTS

| | | | |
|---|---|---|---|
| 2,505,358 | 4/1950 | Gusberg et al. | 128/751 |
| 3,565,062 | 2/1971 | Kuris | 128/303 R |
| 3,749,085 | 7/1973 | Willson et al. | 128/305 |
| 4,445,509 | 5/1984 | Auth | 128/305 |
| 4,479,497 | 10/1984 | Fogarty et al. | 128/344 |
| 4,627,436 | 12/1986 | Leckrone | 128/398 X |
| 4,631,052 | 12/1986 | Kensey | 128/305 X |
| 4,653,496 | 3/1987 | Bundy et al. | 128/751 |
| 4,732,154 | 3/1988 | Shiber | 128/305 |

FOREIGN PATENT DOCUMENTS

| | | | |
|---|---|---|---|
| 163502 | 12/1985 | European Pat. Off. | 128/328 |
| 2804015 | 8/1979 | Fed. Rep. of Germany | 128/305 |
| 1235321 | 6/1971 | United Kingdom | 128/305.1 |
| 2044103 | 10/1980 | United Kingdom | 128/305 |

*Primary Examiner*—Michael H. Thaler

[57] ABSTRACT

An atherectomy catheter is advanced over a guide wire in the anterograde direction to the site of an arterial stenosis. The distal end of the catheter is centered around the guide wire which has been previously advanced through the stenotic lumen. The catheter is then advanced over the guide wire with its sharpened distal end cutting through the stenosis. The atherectomy catheter can also employ rotation or vibration or an electrocautery current to enhance the catheter's cutting action. Suction applied at the catheter's proximal end is used to enhance the collection of plaque cut from the stenosis at the catheter's distal end so that the cut plaque enters a single passageway that lies between the outer surface of the guide wire and the inner surface of the cylindrical catheter.

36 Claims, 2 Drawing Sheets

GUIDE WIRE FOLLOWING TUNNELING CATHETER SYSTEM AND METHOD FOR TRANSLUMINAL ARTERIAL ATHERECTOMY

This is a continuation of co-pending application Ser. No. 091,311 filed on 8/31/87, abandoned, which is a continuation of co-pending application Ser. No. 874,140 filed on 6/13/86, abandoned.

FIELD OF THE INVENTION

This invention is generally in the field of catheters to accomplish arterial, transluminal atherectomy and more specifically, is a guide wire following system for tunneling a lumen through an arterial stenosis so as to directly increase blood flow or as a precursor to balloon angioplasty or some other means for increasing arterial blood flow.

BACKGROUND OF THE INVENTION

Atherosclerotic arterial disease is the leading cause of morbidity and mortality in the United States and most other developed countries. Atherosclerosis is a chronic disease process characterized by lipid deposits and fibrosis of the intima, irregularly distributed in large and medium sized arteries. The disease is progressive and most often becomes clinically manifest in the middle-aged and elderly. When severe, the atherosclerotic plaque causes a reduction of the cross-sectional area of the arterial lumen, with and without thrombosis. Resultant ischemic manifestations include: angina pectoris, myocardial infarction, stroke, intermittent claudication, gangrene of the lower extremities and renovascular hypertension.

The current management of atherosclerotic disease includes preventative therapy aimed at minimizing known major risk factors such as hypertension, smoking, hypercholesterolemia and diabetes mellitus.

Coronary artery bypass grafting (CABG), carotid endarterectomy and bypass grafting (autogenous vein or synthetic graft) of the iliac, femoral and renal arteries are all well established surgical methods of palliative therapy. Although these procedures are often effective in relieving ischemia, each of these represents a major surgical operation with significant associated morbidity, mortality and expense. CABG, for example, requires the opening of the chest cavity (thoracotomy) and use of cardiopulmonary bypass, with not uncommon postoperative complications including postperiocardotomy syndrome, Non-A Non-B hepatitis, stroke and a mortality of approximately one percent (1%) at most medical centers.

Percutaneous transluminal angioplasty (PTA) by means of a balloon catheter is a relatively new ("non-surgical") procedure with proven efficacy in relief of atherosclerotic obstruction of the coronary, renal and peripheral circulations. The technique involves the percutaneous passage (under local anesthesia) of a specialized balloon-tipped catheter through the site of arterial narrowing, and inflation of the balloon to reduce obstruction. This is always done in conjunction with angiographic visualization of the vessel being treated. When successful, this procedure results in a reduction of the arterial stenosis and a decrease in the transstenotic pressure gradient. The mechanism of action is felt to consist of some combination of plaque compression, intimal splitting and medial/adventitial stretching. Healing of the balloon-damaged plaque may involve fibrosis and retraction of the split intimal elements, with further luminal enlargement in the weeks to months following the procedure.

The safety and efficacy of PTA is a function of the vessel being treated, patient selection, and the expertise of the physician performing the procedure. Primary angiographic success, defined as a 20% or greater reduction of stenosis, is now achieved in approximately 80-90% of attempts in carefully selected patients at experienced centers. The obvious advantage of PTA, compared to surgical palliative therapy, is that it does not require major surgery or general anesthesia with the associated sequelae.

Despite its proven efficacy in the palliation of obstructive atherosclerotic disease, PTA, as it is currently performed, has several important technical limitations. These limitations are particularly true in the application of PTA to the coronary circulation.

Even in the most skilled hands, dilation of an arterial obstruction is currently not achievable in approximately 20% of attempts. The most common cause of failed PTA is the inability to pass either the guide wire or dilating catheter through the site of a tight or eccentric stenosis. This problem is even more common in attempts to dilate the difficult to access right and circumflex coronary arteries. Although technical advances, such as steerable catheters, have reduced the frequency of unsuccessful attempts, inability to cross a tight, eccentric or fully closed stenosis remains a major limitation of PTA.

Attempts at balloon or guide wire passage in vessels which are tightly stenotic may lead to arterial dissection and/or acute occlusion necessitating emergency vascular surgery. This major complication occurs in 6-8% of attempts at coronary angioplasty.

Inability to dilate an obstruction, even after proper balloon positioning and inflation is a second common mode of PTA failure. This problem is most frequently encountered in older plaques which are densely fibrotic and/or calcified.

Restenosis of the obstructed arterial segment following successful PTA is a major problem with the current technique. This problem is more common following PTA of a coronary obstruction (30-35% at one year) than in the peripheral circulation (10-15% at two years). Pharmacologic attempts to reduce the incidence of restenosis have been largely unsuccessful.

Distal embolization of atherosclerotic plaque following balloon PTA occurs in approximately 5% of patients undergoing PTA of lower extremity or renal arteries. Although these emboli are usually clinically insignificant in these vascular territories, such embolization could be catastrophic in the cerebral circulation. For this reason, balloon PTA is considered to be constraindicated for the treatment of obstructive lesions in the arteries of the aortic arch, such as the carotid artery.

In U.S. Pat. No. 4,207,874 (dated June 17, 1980) D. S. J. Choy describes a means for using a laser beam to tunnel though an arterial occlusion by vaporization of the obstruction. The difficulty with Choy's invention is that that there is insufficient means to prevent simultaneous destruction of the arterial wall. For example, the Choy invention shows an intense laser beam directed in the forward direction without significant beam attenuation in that direction. If the artery were to curve and the arterial wall was exposed to the laser beam, the wall could also be vaporized which could be catastrophic for the patient. Although the Choy invention describes a means for direct visualization of the obstructed region, it does not describe a centering means or a guide wire following means in order to guarantee that the laser beam does not illuminate part of the arterial wall. Furthermore, the Choy invention may completely obstruct a partially obstructed artery thereby cutting off blood flow to distal tissues for a significant time period. The result is ischemia which could cause irreparable damage to heart or brain tissue.

In U.S. Pat. No. 4,273,128 (date June 16, 1981) B. G. Larry describes a "Coronary Cutting and Dilating Instrument" used for operating a coronary stenosis that is restricting blood flow. The device described by Lary could not be used in a completely or nearly completely occluded artery because its "blunt ovoid tip" could not pass through a completely occluded vessel. Furthermore, the Lary invention does not have any means to prevent its cutting blade from cutting through the arterial wall as well as occluding the stenotic material. Furthermore, there is no means taught in the Lary patent for centering the cutting blade within the arterial walls. Thus, if the probe wire 13 (of FIG. 10) of the Lary invention guides the knife through a highly eccentric lumen within the stenotic plaque its knife blade would surely cut through the arterial wall which would have serious adverse effects for the patient.

In the *Research Resources Reporter,* September 1984, Vol. VIII, No. 9 published by the U.S. Department of Health and Human Services, National Institutes of Health, Margaret Patlak published an article entitled, "Balloon Catherization Opens Totally Blocked Coronary Arteries." This article describes how it is possible to push guide wires through the comparatively soft, center section of an essentially fully occluded artery. Once the guide wire can be pushed through, it was reported that 31 or 45 patients were then able to have a balloon catheter pushed through. Subsequent balloon dilation increased blood flow in each of the 31 patients. However, it would be of considerable value if the 14 patients (27% of the cases) whose stenoses were too tight to allow the passage of the balloon catheter were able to be treated by some means other than surgery. The present invention is related to but different from a prior invention described in a previous patent application, Ser. No. 694,746, now abandoned, filed on Jan. 25, 1985 by Robert E. and Tim A. Fischell which is entitled "A Tunneling Catheter System for Transluminal Arterial Angioplasty." The prior application envisions a tunneling catheter that references the interior surface of the arterial wall before tunneling a hole in the stenotic plaque. The present invention is considerably simpler in concept in that the cutting edge of the tunneling catheter merely follows a guide wire that has already penetrated the narrowed opening in the stenotic plaque.

Thus, it is the goal of the present invention to eliminate the numerous shortcomings of the prior art in order to provide a device which can safely tunnel a clean hole through a narrow partially occluded or fully occluded arterial stenosis.

SUMMARY OF THE INVENTION

The guide wire tunneling atherectomy catheter system described herein is capable of being advanced within a guiding catheter and over a guide wire until it is in contact with an occlusion that is penetrated by the guide wire. During visualization via biplane fluoroscopy, the tunneling catheter is then advanced into plaque which forms the arterial occlusion. The tunneling catheter is generally in the shape of a hollow cylinder with a sharp cutting edge. A bore cylinder of the plaque is caused to enter an interior volume of the advancing tunneling catheter. The bore cylinder is held in place in that volume by means of a suction applied at the proximal end of the tunneling catheter whose hollow lumen is in fluid communication with the distal end of the catheter. When the tunneling catheter is removed from the body (typically along with the guide wire) the bore cylinder of plaque is also removed, thus opening the arterial lumen.

Several methods are possible to promote cutting by the sharpened distal end which is the cutting edge of the cylindrical tunneling catheter. One method is merely to advance the extremely sharp distal cutting edge; another method is to rotate the tunneling catheter's cutting edge as it is advanced. Another method is to apply a high energy ultrasonic vibration into the tunneling catheter from its proximal end causing the sound energy to be readily transmitted by conduction to the catheter's cutting edge. Another method for deftly cutting through the plaque is by applying an electrocautery alternating current to the cutting edge.

Once a tunnel has been made in the plaque, a balloon angioplasty catheter could be advanced into the partially opened occlusion. The balloon can then be expanded to further dilate the opening as is well known in the art of percutaneous transluminal balloon angioplasty. Another method for enlarging the opening may be by utilizing a second tunneling catheter that has a larger outer diameter than the first used and is specifically designed to center itself in the opening made by the first guide wire following, tunneling catheter. The first tunnel that is bored in the plaque may of itself be of sufficient diameter to allow adequate blood flow without the subsequent use of an angioplasty balloon catheter or an enlarging tunneling catheter.

Thus an object of this invention is to tunnel a hole through an arterial occlusion, particularly an occlusion that is nearly fully or totally occluded or which has a narrowed passageway that is centrally or eccentrically located relative to the center of the arterial lumen.

Another object of the present invention is to employ a sharpened, cylindrical edge of a tunneling catheter to cut through the plaque either by directly pushing on it or by rotating it while advancing its sharpened distal edge through the plaque.

Still another object of the present invention is to utilize ultrasonic vibration of the cylindrical cutting edge to facilitate its ability to cut through the plaque.

Still another object of the present invention is to utilize an electrocautery to apply an electric current to the cutting edge of the tunneling catheter to enhance its ability to cut through the occlusion.

Still another object of this invention is to first use a guide wire following tunneling catheter system to bore a tunnel into the plaque and then use balloon angioplasty to further enlarge the lumen of the stenotic plaque.

Still another object of this invention is to first use a guide wire following tunneling catheter system to bore a tunnel into the plaque and then use a tunneling type of enlarging tool at the catheter's distal end to further enlarge the lumen of the stenotic plaque.

Still another object of the present invention is to apply this technique to any occluded artery including the coronary arteries, the carotoid artery, the renal artery and the arteries of the legs and arms.

DETAILED DESCRIPTION OF THE INVENTION

Figure 1:
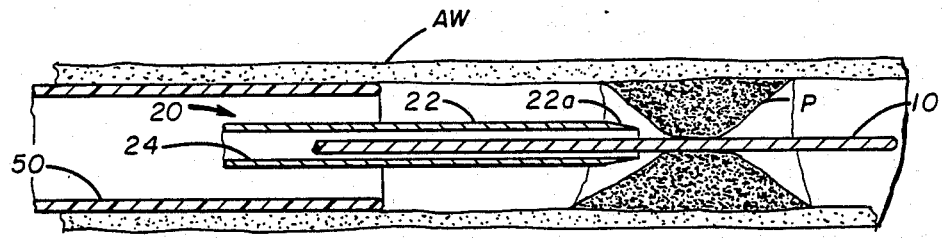

FIG. 1 shows the configuration of the guide wire tunneling catheter 20 at its distal end 22 with the guide wire 10 being shown at it penetrates a narrow stenosis consisting of plaque P within an arterial wall AW. To achieve this condition a guiding catheter 50 would first be placed through the femoral artery in a conventional manner and then advanced in a conventional manner until its distal end lies just proximal to the plaque P. At this point the procedure, the artery would be visualized with image intensified fluoroscopy which should show that the sharpened edge 22a of the distal end 22 of the tunneling catheter 20 is just proximal to the plaque P.

Figure 2:
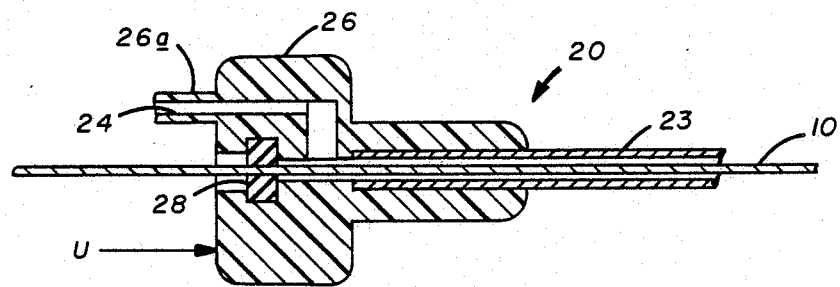

FIG. 2 shows the configuration of the proximal end of the guide wire tunneling catheter 20 as it lies just outside the patient's body. The catheter cylinder's proximal end 23 is joined by a press fit or adhesive into the handle 26. The guide wire 10 is shown penetrating a felt or foam rubber seal 28 that is set into the handle 26. The interior region 24 (of FIGS. 1 and 2) lying between the outer surface of the guide wire 10 and the interior cylindrical surface of the tunneling catheter 20 allows fluid communication between the port 26a and the interior of the catheter's distal end 22. For example, a suction can be applied at the port 26a which suction is communicated to the interior region 24 and then to the catheter's sharpened edge 22a as it is advanced through the plaque P. The port 26a can also be used for injection of a radio-opaque dye to better visualize the stenotic artery.

When fluoroscopy indicates that the sharpened edge 22a is just in contact with the plaque P, then suction is applied simultaneously with advancing the catheter cylinder 22 into the plaque P. Rotating the handle while advancing the tip 22a through the plaque will enhance the cutting action. The rotational motion may optimally be oscillatory. By applying an ultrasonic vibrational input U (as shown in FIG. 2) on the handle 26, the cutting action of the tip 22a will also be enhanced. Also, an electrocautery current applied to the tip 22a (as described in the referenced patent application Ser. No. 694,746) could also be used for enhancing the cutting action of the tip 22a. Then either the entire catheter 20 is removed from the body by itself or preferably it is removed simultaneously with the guide wire 10. The suction is maintained until the entire catheter 20 and guide wire 10 are completely removed from the body. When this is done a small but finite portion of the plaque P is removed thus enlarging the narrow opening of the stenotic plaque P.

Figure 3:
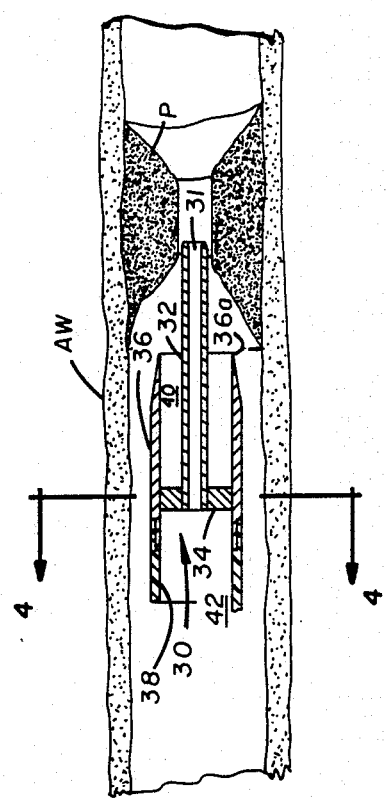

After an initial enlargement has been made by the tunneling catheter 20, a conventional angioplasty balloon catheter (not shown) could have its balloon tip advanced into the enlarged opening and dilated in a conventional manner to further open the stenotic lumen in order to further increase blood flow. However an alternative procedure using an enlarging tunneling catheter as shown in FIG. 3 could be used. FIG. 3 shows just the distal end 36 of such an enlarging catheter 30. FIG. 3 also shows the plaque P after it has had a cylinder bore volume removed by the guide wire following tunneling catheter 20. The interior lumen of the cut plaque P would then be large enough for either conventional balloon dilation or the application of a larger diameter tunneling catheter such as that shown in FIG. 3.

Figure 4:
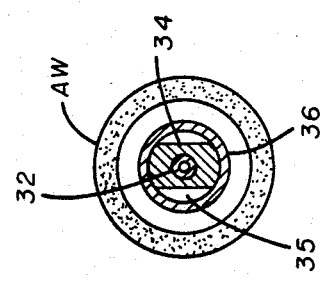

The distal end 36 of the enlarging tunneling catheter 30 would have a sharpened edge 36a and a small diameter central cylinder 32 having an interior lumen 31 which typically surrounds a guide wire (not shown) that is first advanced through a guiding catheter (also not shown) and then advanced into the enlarged interior lumen of the plaque P. Thus the enlarging tunneling catheter 30 is typically advanced along a guide wire (like guide wire 10 of FIG. 1) and within a guiding catheter such as that shown as catheter 50 in FIG. 1. The central cylinder 32 is held along the longitudinal axis of the distal end 36 of the enlarging tunneling catheter 30 by means of a separator 34 that is also shown in cross section in FIG. 4.

Between the interior surface of the distal end 36 and the exterior surface of the central cylinder 32 is an annular chamber 40 that is in fluid communication through holes 35 (see FIG. 4) of the separator 34 with the interior chamber 42 of the enlarging catheter 30 that lies on the proximal side of the separator 34 and within a plastic cylinder 38 that joins outside the body to a handle similar to the handle 26 shown in FIG. 2. Thus a suction applied at the proximal end of the plastic cylinder 38 of the enlarging catheter 30 can be used during the cutting process to hold that portion of the plaque P that can be removed when the sharpened edge 36a is advanced through the plaque P. After that is accomplished, the entire enlarging tunneling catheter 30 can be removed (while still applying suction at its proximal end) without removing the guide wire (not shown) and without removing the guiding catheter (also not shown).

As is the case with the guide wire following tunneling catheter 20 of FIGS. 1 and 2, the cutting action of the enlarging catheter 30 can be accomplished by simply pushing it forward, or manually rotating it while advancing it or by the application of ultrasonic vibration from the proximal end handle as has already been described herein, or by application of an electrocautery current as described in U.S. patent application Ser. No. 694,746.

As far as materials are concerned, the tunneling catheter 20 would typically have a Type 316 stainless steel cylinder 22 and a plastic handle typically made from PVC or acetal. The outer diameter of the cylinder portion of the catheter 20 would typically be 1.0 to 1.5 mm with a wall thickness of approximately 0.1 mm. The guide wire 10 would typically be Teflon coated steel wire with 0.5 mm outside diameter. The guiding catheter 50 would be typically 6 to 12 French depending on the artery into which its distal end would be placed. The entire distal end of the enlarging tunneling catheter 30 would typically be made from Type 316 stainless steel. The outer diameter of the central cylinder 32 (of FIG. 3) would typically be 1.0 to 1.2 mm with 0.15 mm wall thickness. The length of the annular chamber 40 would typically be 1 to 3 cm depending on the length of plaque P that is to be cut. The plastic cylinder 38 would typically be made from PVC. The outer diameter of the enlarging tunneling catheter 30 would be selectable between 2 and 10 mm depending on the particular artery into which it would be advanced. The distal coronary arteries might require a 2 mm diameter. The carotid artery might use a 10 mm diameter enlarging tunneling catheter.

Various other modifications, adaptations and alternative designs are of course possible in light of the above teachings. Therefore, it should be understood at this time that within the scope of the appended claims, the invention may be practiced otherwise than as specifically described therein.

What is claimed is:

1. A guide wire following tunneling catheter system for percutaneous transluminal atherectomy, comprising:
   a guide wire with distal and proximal ends and adapted to be advanced within a patient's arterial system and to penetrate through an arterial stenosis;
   a tunneling catheter with distal and proximal ends having for most of its length a single, thin walled, cylindrical tube with a single inner cylindrical surface extending for most of the length of said tunneling catheter, said inner cylindrical surface being adapted to fit around said guide wire so that said tunneling catheter can be advanced along said guide wire to said arterial stenosis, and wherein a passageway is formed between said inner cylindrical surface of said tunneling catheter and the outer surface of said guide wire, said passageway being in fluid communication between said distal and proximal ends of said tunneling catheter, said distal end of said tunneling catheter including a centering means operably attached to said tunneling catheter for centering the distal end of said tunneling catheter around said guide wire and within the interior passageway of the stenosis, wherein said centering means is a centering cylindrical member whose outer diameter is smaller than that of said tunneling catheter, wherein the distal end of said centering cylindrical member extends out from the distal end of said tunneling catheter and wherein the proximal end of said centering cylindrical member is operably attached to said distal end of said tunneling catheter; and,
   a cutting means located near the distal end of said tunneling catheter for cutting through said arterial stenosis as said tunneling catheter is advanced along guide wire.

2. The catheter system of claim 1, further comprising a separator member that is secured within the interior lumen of said distal end of said tunneling catheter wherein the interior surface of said distal end of said tunneling catheter and the external surface of said centering cylindrical member means forms an annular chamber, and wherein said separator member includes at least one hole allowing said annular chamber to be in fluid communication with said interior lumen of said tunneling catheter.

3. The catheter system of claim 1, wherein said proximal end of said tunneling catheter is adapted to extend external to said patient and wherein said proximal end of said tunneling catheter is operably coupled to a suction means located external to said patient, for applying suction to said interior lumen for drawing out portions of plaque into said interior lumen.

4. The catheter system of claim 1, wherein said proximal end of said tunneling catheter is adapted to extend external to said patient and wherein said proximal end of said tunneling catheter is operably coupled to a fluid injection means located external to said patient for injecting a fluid through said interior lumen into the vicinity of said arterial stenosis.

5. The catheter system of claim 1 wherein said cutting means is a sharpened edge forming a mouth at the distal end of said tunneling catheter.

6. The catheter system of claim 5, wherein said sharpened edge is a cylindrical cutting edge for cutting a cylindrical bore of plaque from said arterial stenosis.

7. The catheter system of claim 1, wherein said tunneling catheter and said centering cylindrical member are fixedly attached in such a way as to allow creation of at least one hole between said tunneling catheter and said centering cylindrical member thus allowing fluid communication between said interior lumen of said tunneling catheter and the interior of the artery undergoing atherectomy.

8. The catheter system of claim 1, wherein said cutting means has at least one sharpened edge forming at least one mouth at the distal end of said tunneling catheter.

9. A guide wire following catheter system for percutaneous transluminal atherectomy, comprising:
   a guide wire with distal and proximal ends, and adapted to be advanced within a patient's arterial system and to penetrate through an arterial stenosis, said guide wire being essentially flexible throughout its length that lies within the stenotic artery and being free of any substantial protuberance at its said distal end; and
   a tunneling catheter with distal and proximal ends and having for most of its length a single, thin wall tube having an outer cylindrical surface and an inner cylindrical surface, said inner cylindrical surface forming an interior lumen and being adapted to fit around said guide wire so that said tunneling catheter can be advanced along said guide wire to said arterial stenosis; and,
   a cutting means located at the distal portion of said tunneling catheter for cutting through said arterial stenosis as said tunneling catheter is advanced along said guide wire, said cutting means having at least one cutting edge and having at least one opening into which the cut plaque enters as said cutting means is advanced through the stenotic plaque, and wherein none of said cutting edges extends outward from said outer cylindrical surface of said tunneling catheter and wherein said cutting means is precluded from cutting through said guide wire during rotation of said tunneling catheter as a result of said inner cylindrical surface of said tunneling catheter being a smooth cylindrical surface and being free of a cutting edge which could cut through said guide wire and wherein the inner diameter of said distal end of said tunneling catheter is only slightly larger than the outside diameter of said guide wire so that said distal end of said tunneling catheter is substantially centered about said guide wire; and wherein said tunneling catheter has a passageway formed between said inner cylindrical surface of said tunneling catheter and the outer surface of said guide wire, said passageway being in fluid communication between said distal and proximal ends of said tunneling catheter and being a means for collecting and removing cut plaque as said cutting means is advanced over said guide wire so as to cut the stenotic plaque.

10. The catheter system of claim 9, wherein said proximal end of said tunneling catheter is adapted to extend external to said patient and is operably coupled to a suction means located external to said patient for applying suction to said passageway for drawing cut portions of plaque into said passageway.

11. The catheter system of claim 9, wherein said proximal end of said tunneling catheter is adapted to extend external to said patient and is operably coupled to a fluid injection means located external to said patient for injecting a fluid through said passageway into the vicinity of said arterial stenosis.

12. The catheter system of claim 11, wherein said fluid is a radio-opaque dye.

13. The catheter system of claim 9 wherein said proximal end of said tunneling catheter is adapted to extend external to said patient and is operably coupled to a rotary driving means located external to said patient for applying rotational motion to said cutting means of said tunneling catheter so as to enhance the cutting of the plaque.

14. The catheter system of claim 9 wherein said proximal end of said tunneling catheter is adapted to extend external to said patient and is operably coupled to a source of electrocautery current means located external to said patient for applying an electrocautery current to siad cutting means of said tunneling catheter so as to enhance the cutting of the plaque by applying a high density electric current through the tissue that is being cut.

15. The catheter system of claim 9 wherein said proximal end of said tunneling catheter is adapted to extend external to said patient and is operably coupled to an ultrasonic vibration means located external to said patient for applying mechanical vibration to said cutting means of said tunneling catheter so as to enhance the cutting of the plaque.

16. The catheter system of claim 9, wherein said cutting means is a sharpened edge forming a mouth at the distal end of said tunneling catheter.

17. The catheter system of claim 16, wherein said sharpened edge is a cylindrical cutting edge for cutting a cylindrical bore of plaque from said arterial stenosis.

18. The catheter system of claim 9, wherein said proximal ends of both said tunneling catheter and said guide wire are adapted to extend external to said patient and wherein said catheter system further comprises:
  a control handle fixedly attached to the proximal end of said tunneling catheter, said control handle having a hollow interior portion that is in communication with the interior lumen of said tunneling catheter;
  a first entry into said hollow interior portion of said control handle having a sealing means for forming a seal around a section of said guide wire, said sealing means permitting said control handle and said tunneling catheter to be moved longitudinally along said guide wire; and,
  a second entry into said hollow interior portion of said control handle adapted to form a port in fluid communication with said interior lumen of said tunneling catheter.

19. The catheter system of claim 9 further comprising a guiding catheter having an interior lumen and adapted to be advanced within said patient's arterial system to the site of said arterial stenosis, wherein said guide wire and said tunneling catheter are adapted to be advanced through said guiding catheter to the site of said arterial stenosis.

20. The catheter of claim 9 wherein said guide wire cooperates with said inner cylindrical surface of said tunneling catheter at its distal end so as to limit the radial displacement of said cutting means so as to center said cutting means about the lumen of the stenosis.

21. A guide wire following tunneling catheter system for percutaneous transluminal atherectomy, comprising:
  a guide wire with distal and proximal ends, and adapted to be advanced within a patient's arterial system and to penetrate through an arterial stenosis, said guide wire being essentially flexible throughout its length that lies within the stenotic artery; and
  a tunneling catheter with distal and proximal ends and having for most of its length a single, thin walled tube having an outer cylindrical surface and an inner cylindrical surface, said inner cylindrical surface forming an interior lumen and being adapted to fit around said guide wire so that said tunneling catheter can be advanced along said guide wire to said arterial stenosis; and
  a cutting means located at the distal portion of said tunneling catheter for cutting through said arterial stenosis as said tunneling catheter is advanced along said guide wire, said cutting means having at least one cutting edge and having at least one opening into which the cut plaque enters as said cutting means is advanced through the stenotic plaque; and wherein said tunneling catheter has a passageway formed between said inner cylindrical surface of said tunneling catheter and the outer surface of said guide wire, said passageway being in fluid communication between said distal and proximal ends of said tunneling catheter and being a means for collecting and removing the cut plaque as said cutting means is advanced over said guide wire so as to cut the stenotic plaque; and wherein said tunneling catheter has a radial motion restraining means at its most distal extremity for limiting the radial motion of said cutting means relative to said guide wire, said radial restraining means having a cylindrical hole, the diameter of said hole being substantially smaller than the diameter of said inner cylindrical surface of said tunneling catheter and said hole having a smooth interior cylindrical surface to prevent said cutting means from cutting said guide wire during rotation of said tunneling catheter, and said hole being sized to form a sliding fit over said guide wire so as to center said distal end of said cutting means around said guide wire as said cutting means is advanced through the stenotic plaque.

22. The catheter system of claim 21, wherein said tunneling catheter is operably attached to a rotating means at its proximal end for rotating said tunneling catheter as it is advanced over said guide wire in order to facilitate the cutting action of said cutting means as the distal end of said tunneling catheter is advanced over said guide wire and through said arterial stenosis.

23. The catheter system of claim 21, wherein said at least one cutting edge bores a cylindrical hole through the plaque of said arterial stenosis.

24. The catheter system of claim 21, wherein said tunneling catheter is rotated within a guiding catheter as said cutting means at said distal portion of said tunneling catheter is advanced along said guide wire and through said arterial stenosis.

25. The catheter system of claim 21, wherein said tunneling catheter is coupled to an ultrasonic vibration means so as to mechanically vibrate the distal end of said tunneling catheter as it is advanced through said arterial stenosis.

26. The catheter system of claim 21, wherein a high density electrocautery current is applied through the plaque as said tunneling catheter is advanced through said arterial stenosis.

27. The catheter system of claim 21, wherein said proximal end of said tunneling catheter is adapted to extend external to said patient and is operably coupled to a suction means located external to said patient for applying suction to said passageway for drawing cut portions of plaque into said passageway.

28. The catheter system of claim 21, wherein said proximal end of said tunneling catheter is adapted to extend external to said patient and is operably coupled to a fluid injection means located external to said patient for injecting a fluid through said passageway into the vicinity of said arterial stenosis.

29. A percutaneous transluminal atherectomy procedure comprising the steps of:
advancing a guide wire with distal and proximal ends through a patient's arterial system and penetrating through an arterial stenosis, said guide wire being essentially flexible throughout that portion of its length that lies within the stenotic artery and being free of any substantial protuberance at its said distal end;
advancing a tunneling catheter with distal and proximal ends over said guide wire, said tunneling catheter having for most of its length a single, thin walled, cylindrical tube having an outer cylindrical surface and an inner cylindrical surface, said inner cylindrical surface forming an interior lumen and being adapted to fit around said guide wire thus forming a passageway between said inner cylindrical surface of said tunneling catheter and the outer surface of said guide wire and having said outer cylindrical surface of said tunneling catheter free of protuberances wherever it lies within the arterial system, said distal end of said tunneling catheter including a centering means operably attached to said tunneling catheter for centering the distal end of said tunneling catheter around said guide wire and within the interior passageway of the stenosis, wherein said centering means is a centering cylindrical member whose outer diameter is substantially smaller than the outer diameter of said tunneling catheter, wherein the distal end of said centering cylindrical member extends out from the distal end of said tunneling catheter and wherein the proximal end of said centering cylindrical member is operably attached to said distal end of said tunneling catheter;
advancing a cutting means located at the distal portion of said tunneling catheter through said arterial stenosis as said tunneling catheter is advanced along said guide wire, said cutting means having at least one cutting edge and having at least one opening into which the cut plaque enters as said cutting means is advanced through the stenotic plaque; and having none of said cutting edges extending outward from said outer cylindrical surface of said tunneling catheter; and
collecting and removing the cut plaque as said cutting means is advanced over said guide wire so as to cut through said arterial stenosis.

30. The procedure of claim 29, further comprising the step of:
applying suction to the proximal end of said tunneling catheter, thereby drawing plaque cut by said cutting means into said interior lumen.

31. The procedure of claim 29, further comprising the step of:
applying a rotational motion to said tunneling catheter as it is advanced through the stenotic plaque.

32. The procedure of claim 29, further comprising the step of:
applying an ultrasonic vibration to said tunneling catheter to enhance the cutting action of its distal sharpened edge.

33. The procedure of claim 29, further comprising the step of:
applying an electrocautery current to said tunneling catheter to enhance its cutting action by applying a high density electric current to the tissue that is being cut.

34. The procedure of claim 29, further comprising the step of:
advancing and later retracting said tunneling catheter through a guiding catheter that is placed within the arterial lumen.

35. The procedure of claim 29, further comprising the step of:
using conventional percutaneous transluminal balloon angioplasty to further dilate the stenotic lumen after a guide wire following tunneling catheter was used for the initial removal of some stenotic plaque.

36. A guide wire following tunneling catheter system for percutaneous transluminal atherectomy, comprising:
a guide wire with distal and proximal ends and adapted to be advanced within a patient's arterial system and to penetrate through an arterial stenosis;
a tunneling catheter with distal and proximal ends and having for most of its length a single, thin walled, cylindrical tube having an outer cylindrical surface and an inner cylindrical surface, said inner cylindrical surface forming an interior lumen being adapted to fit around said guide wire thus forming a passageway between said inner cylindrical surface and the outer surface of said guide wire and having said outer cylindrical surface of said tunneling catheter free of protuberances wherever it lies within the arterial system, said tunneling catheter being capable of being advanced along said guide wire to said arterial stenosis, said distal end of said tunneling catheter including a centering means operably attached to said tunneling catheter for centering the distal end of said tunneling catheter around said guide wire and within the interior passageway of the stenosis, wherein said centering means is a centering cylindrical member whose outer diameter is substantially smaller than the outer diameter of said tunneling catheter and whose inner diameter is sized to be just slightly larger than the outside diameter of said guide wire so as to move slideably along said guide wire;
a cutting means located near the distal end of said tunneling catheter for cutting through said arterial stenosis as said tunneling catheter is advanced along said guide wire;
a suction means operably attached to said tunneling catheter at its proximal end which is adapted to extend external to said patient; and,
a rotating means operably attached to said tunneling catheter at its proximal end which is adapted to extend external to the patient for rotating said tunneling catheter while simultaneously applying suction and advancing said tunneling catheter over said guide wire and through said arterial stenosis.

* * * * *